(12) United States Patent
Bonnette et al.

(10) Patent No.: US 7,842,010 B2
(45) Date of Patent: Nov. 30, 2010

(54) PNEUMATICALLY-OPERATED THROMBECTOMY CATHETER DEPLOYMENT SYSTEM

(75) Inventors: Michael John Bonnette, Minneapolis, MN (US); Arun Saini, Burnsville, MN (US); Ernest Ralph Scherger, III, Center City, MN (US); Eric Joel Thor, Arden Hills, MN (US); Stephen Earl Weisel, Montrose, MN (US)

(73) Assignee: MEDRAD, Inc., Indianola, PA (US)

( * ) Notice: Subject to any disclaimer, the term of this patent is extended or adjusted under 35 U.S.C. 154(b) by 336 days.

(21) Appl. No.: 11/294,005

(22) Filed: Dec. 5, 2005

(65) Prior Publication Data

US 2007/0129679 A1    Jun. 7, 2007

(51) Int. Cl.
*A61M 37/00* (2006.01)
*F04B 17/00* (2006.01)
*B65D 81/24* (2006.01)

(52) U.S. Cl. ................. 604/131; 417/392; 206/210
(58) Field of Classification Search ............. 604/151, 604/152, 153, 154; 417/395, 396, 397
See application file for complete search history.

(56) References Cited

U.S. PATENT DOCUMENTS

| 2,464,283 | A | * | 3/1949 | Adams ................... 91/421 |
| 3,598,727 | A | * | 8/1971 | Willock ................. 210/177 |
| 3,700,360 | A | * | 10/1972 | Shaddock ............... 417/404 |
| 4,065,230 | A | * | 12/1977 | Gezari .................. 417/317 |
| 4,119,113 | A | * | 10/1978 | Meginniss, III ........... 137/99 |
| 4,158,530 | A | * | 6/1979 | Bernstein ............... 417/389 |
| 4,778,356 | A | * | 10/1988 | Hicks .................. 417/397 |
| 4,821,761 | A | * | 4/1989 | Aid et al. ............. 137/101.21 |
| 4,865,067 | A | * | 9/1989 | Duquette ................ 137/4 |
| 4,892,279 | A | * | 1/1990 | Lafferty et al. ........... 248/125.8 |
| 4,925,444 | A |   | 5/1990 | Orkin et al. |
| 5,487,649 | A | * | 1/1996 | Dorsey et al. ............ 417/395 |
| 5,529,463 | A | * | 6/1996 | Layer et al. ............. 417/403 |
| 5,536,242 | A | * | 7/1996 | Willard et al. ............ 604/30 |
| 5,827,229 | A |   | 10/1998 | Auth et al. |
| 5,879,361 | A |   | 3/1999 | Nash |
| 6,676,627 | B1 | * | 1/2004 | Bonnette et al. ........... 604/22 |
| 6,695,803 | B1 |   | 2/2004 | Robinson et al. |

(Continued)

OTHER PUBLICATIONS

Beasley, Albert Jr. Fluid Power, Jul. 1990, Naval Education and Training Program Management Support Activity. Ch. 6, p. 20.*

(Continued)

*Primary Examiner*—Kevin C Sirmons
*Assistant Examiner*—William Carpenter
(74) *Attorney, Agent, or Firm*—David Schramm

(57) ABSTRACT

A pneumatically-operated thrombectomy catheter deployment system having a plurality of components collectively acting as a drive unit, including a double-acting air cylinder, a reciprocating assembly including a positionable four-way valve, a high pressure pump, an effluent pump, a compressed air tank, and other closely related components. The double-acting air cylinder is reciprocatingly driven by the complement of the drive unit components to provide high pressure saline for use in the thrombectomy catheter and to exhaust effluent from the system. A plurality of preconnected components are connected to the drive unit including a thrombectomy catheter, a saline supply bag, an effluent collection bag, connection tubes, and other closely related components.

20 Claims, 6 Drawing Sheets

U.S. PATENT DOCUMENTS

| | | | |
|---|---|---|---|
| 6,719,717 B1 | 4/2004 | Johnson et al. | |
| 6,936,056 B2 * | 8/2005 | Nash et al. | 606/159 |
| 7,179,269 B2 * | 2/2007 | Welch et al. | 606/159 |
| 2001/0049486 A1 * | 12/2001 | Evans et al. | 604/4.01 |
| 2004/0069709 A1 * | 4/2004 | Brugger et al. | 210/646 |
| 2004/0230212 A1 * | 11/2004 | Wulfman | 606/167 |
| 2007/0073233 A1 * | 3/2007 | Thor et al. | 604/151 |
| 2007/0129679 A1 | 6/2007 | Bonnette | |

OTHER PUBLICATIONS

International Search Report issued in corresponding International Patent Application PCT/US06/36684.

ANGIOJET Product Manual, Possis Medical, Inc., May 7, 2005.

"Design Stars" Teague, P., Design News, Nov. 8, 2004.

* cited by examiner

follows (assuming the drive unit is on):
PNEUMATICALLY-OPERATED THROMBECTOMY CATHETER DEPLOYMENT SYSTEM

CROSS REFERENCES TO RELATED APPLICATIONS

This patent application is related to patent application Ser. No. 11/237,558 filed Sep. 28, 2005, entitled "Thrombectomy Catheter Deployment System", which is pending.

BACKGROUND OF THE INVENTION

1. Field of the Invention

In the human body, blockages in blood vessels, arteries and the like often oppose the free flow of blood therein, one such blockage of which is thrombus. Thrombus is coagulated blood that is developed in vivo. Thrombus blocks blood flow to living tissue leading to ischemia and eventually tissue death. Depending on the end organ and the amount of blocked blood flow, the effects of thrombus can range from unnoticeable to death. Thrombus residing in a variety of native vessels and grafts can be treated. The occurrence and presence of thrombus occurs in several ways. First, it occurs in coronary procedures where thrombus is associated with myocardial infarction or heart attack. Thrombus is also common in older saphenous vein bypass grafts. Second, peripheral artery interventional procedures can encounter thrombus as well. The use of synthetic grafts and stents for the treatment of peripheral arterial disease can produce thrombus as a result of blood material interactions. Furthermore, thrombus can be formed resulting from the progression of the peripheral artery disease itself. As the artery becomes blocked with atherosclerotic material, thrombus can result as blood passes through the restricted diseased vessel. Venous thrombus can result from either vessel injury or hypercoagulable blood chemistry. Finally, interventional procedures themselves can create thrombus. Access to the patient's arterial vascular system is commonly accomplished via a femoral artery puncture. At the end of the procedure, the puncture site must be closed by either applying pressure until a natural thrombotic plug forms or using an arterial closure product which typically uses some sort of collagen plug or suture. In either case, thrombus can form at the puncture site and move down the femoral artery. Furthermore, during the interventional procedure itself, foreign materials such as catheters and guidewires are introduced into the patient's blood stream. The patient needs anticoagulants, typically heparin, to prevent the occurrence of thrombus. On occasion, inattention to activated clotting times can result in the occurrence of thrombus during the procedure. Third, other parts that have been treated by thrombectomy catheters include arterial-venous access grafts for hemodialysis patients. Thrombectomy catheters have proven effective in opening these grafts that occasionally become blocked with thrombus. Thrombectomy catheters have also been used in the venous system for deep vein thrombosis and occasionally in neurological venous applications. Finally, thrombectomy catheters have been clinically investigated in neurological arterial applications as well. In general, thrombectomy catheters have a potential application wherever thrombus forms in native arteries, veins and grafts. Having developed such thrombectomy catheters, there exists a need for a deployment system to allow simple and rapid use of a thrombectomy catheter and the devices supporting use of the thrombectomy catheter.

2. Description of the Prior Art

Current thrombectomy catheter utilization devices consist of a drive unit, disposable components including a variety of sterile thrombectomy catheters, a transportable sterile pump, bubble detectors, a saline supply tube/bag spike assembly, a nonsterile waste or effluent collection bag, and other associated components. Often, the use of such devices is overall cumbersome involving a large number of setup steps required for preparation and use. The current setup steps are roughly as follows (assuming the drive unit is on):

(1) open sterile package for the pump set;
(2) do a sterile exchange to hand off the catheter connection end of the pump supply line to the sterile technician;
(3) preclamp a Roberts clamp for the saline supply tube line;
(4) load the pump into the capture block while simultaneously loading the pump piston head into a reciprocating ram;
(5) spike a heparinized bag of saline;
(6) install the saline supply tube into an inlet bubble detector;
(7) unclamp the bag spike Roberts clamp to enable the pump to become primed;
(8) open the effluent collection bag packaging and remove the effluent collection bag;
(9) attach the effluent return tube to the proximal end of the pump supply line effluent connection;
(10) hang the effluent collection bag on the side of the drive unit;
(11) install the effluent waste tube through the roller pump;
(12) close the roller pump cover;
(13) push the effluent waste tube into the outlet bubble detector just proximal to the roller pump;
(14) select the catheter mode on the drive unit;
(15) open the catheter sterile packaging;
(16) do a sterile exchange to hand off the entire catheter to the sterile technician;
(17) connect the high pressure connection from the pump supply line to the catheter;
(18) connect the effluent Luer connection from the supply line to the catheter; and,
(19) submerge the catheter tip in a bowl of sterile saline and operate a drive unit foot switch to prime the catheter.

Compare this to the pneumatically-operated thrombectomy catheter deployment system, the present invention, having a plurality of preconnected components wherein the setup consists of:

(1) opening a sterile package containing the pneumatically-operated thrombectomy catheter deployment system for the thrombectomy catheter;
(2) doing a sterile exchange to hand off the catheter portion to the sterile technician;
(3) attaching an air line to catheterization lab pressured gas source if the onboard compressed air tank is not utilized;
(4) spiking a heparinized saline bag;
(5) priming the pump; and,
(6) submerging the catheter tip in sterile saline and priming the catheter.

Current generation drive units have been sequentiality built into the setup steps. The drive unit must turn on and go through self-test prior to placing the pump into the capture block. The pump must be loaded prior to spiking the saline supply bag, etc. Compare this to the instant invention wherein the pneumatically-operated thrombectomy catheter system, which is preconnected, requires no loading of a pump or connection of multiple components by tubing and the like except only for spiking of a saline supply bag. The only step that requires sequentiality is priming the catheter after the saline supply bag is spiked.

Current thrombectomy catheter utilization devices involve substantially a two-handed installation maneuver whereby a pump body is aligned within a capture block in the drive unit while a piston head of the pump is simultaneously loaded into a receptor in a reciprocating linear actuator. Each manual maneuver requires devoted attention and coordination by the operator. Contrast this to the pneumatically-operated thrombectomy catheter deployment system, the present invention, having preconnected components, wherein a preconnected drive unit, a preconnected thrombectomy catheter, and a preconnected effluent collection bag and preconnected compressed air tank, as well as preconnected tubing and the like, are simply placed on a medical equipment stand without any extraordinary effort by the operator.

SUMMARY OF THE INVENTION

The general purpose of the present invention is to provide a pneumatically-operated thrombectomy catheter deployment system.

According to one or more embodiments of the present invention, there is provided a pneumatically-operated thrombectomy catheter deployment system. The invention provides a sterile prepackaged, preconnected and disposable low cost self-contained device for use in thrombectomy or other related procedures. The invention is pneumatically-operated by a compressed air tank which makes portable operation feasible and is regulated to eliminate hospital-to-hospital variation in supply gas pressure. The invention is operable where no compressed air source is available, or alternatively, the invention can be incorporated into use using stationary hospital or operating room air supply sources in lieu of the compressed air tank. A drive unit is central to operation of the invention having major components consisting of a double-acting air cylinder, a reciprocating assembly which influences the operation of a four-way valve, a four-way valve which influences the directional operation of the double-acting air cylinder, a high pressure pump which is operated by the double-acting air cylinder, and an effluent pump opposing the high pressure pump, both of which are operated by the double-acting air cylinder. The use of the effluent pump allows isovolumetric flow where waste outflow equals saline inflow into a patient. Saline is made available to the high pressure pump drive unit from a spiked saline supply bag, wherein one end of the saline supply tube is preconnected to the high pressure pump. Accordingly, a high pressure saline delivery tube is preconnected between the high pressure pump and the manifold of a preconnected thrombectomy catheter in order to provide for useful ablative cross stream flows which emanate from the distal portion of the thrombectomy catheter. An effluent tube is preconnected between the manifold of the thrombectomy catheter and a manifold input of the effluent pump, and accordingly another effluent tube connects between the manifold output of the effluent pump and the effluent collection bag.

The double-acting air cylinder is reciprocatingly operated by compressed air made available alternately to opposing ends of the double-acting air cylinder to drive the piston thereof first in one direction and then in the other direction. Such alternatingly supplied compressed air is supplied by the interaction of the reciprocating assembly with top and bottom return actuators of the four-way valve which delivers compressed air to and which vents previously utilized air from the air cylinder. Reciprocating operation of the air cylinder operates opposed pumps including a high pressure pump and an effluent pump aligned at opposite ends of the double-acting air cylinder. When one pump is admitting liquid, the other pump is forcibly expelling fluid during actuation of the double-acting air cylinder in one particular direction; i.e., when the high pressure pump is forcibly expelling fluid under high pressure, the effluent pump is suctionally receiving effluent, and when the high pressure pump is suctionally receiving supply saline, the effluent pump is forcibly expelling effluent under pressure.

One significant aspect and feature of the pneumatically-operated thrombectomy catheter deployment system, the present invention, is that it is prepackaged in a sterile enclosure and is disposable.

One significant aspect and feature of the pneumatically-operated thrombectomy catheter deployment system is the elimination of the need for a hospital to make a large capital investment for an expensive and complicated stationary drive unit;

One significant aspect and feature of the pneumatically-operated thrombectomy catheter deployment system is that it is small and portable enough to be suspended from an IV pole.

One significant aspect and feature of the pneumatically-operated thrombectomy catheter deployment system is that it can be fashioned with a minimum number of components.

One significant aspect and feature of the pneumatically-operated thrombectomy catheter deployment system is that it utilizes compressed air from a small compressed air tank or canister or, alternatively, from stationary hospital, clinic or other air supplies.

One significant aspect and feature of the pneumatically-operated thrombectomy catheter deployment system is that it uses a double-acting air cylinder for simultaneous reciprocating operation of a high pressure pump and an effluent pump in opposite directions.

One significant aspect and feature of the pneumatically-operated thrombectomy catheter deployment system is the provision of a high pressure pump which opposes an effluent pump about a double-acting air cylinder.

One significant aspect and feature of the pneumatically-operated thrombectomy catheter deployment system is the incorporation of a reciprocating assembly to alternately position opposed actuators of a four-way valve.

Another significant aspect and feature of the pneumatically-operated thrombectomy catheter deployment system is the provision and use of a four-way valve to supply compressed air to one side of a double-acting air cylinder while at the same time venting the remaining side of such double-acting air cylinder.

Another significant aspect and feature of the pneumatically-operated thrombectomy catheter deployment system is the provision of two opposing pumps arranged such that one pump is compressingly expelling fluid while the opposed pump is receiving fluid.

Another significant aspect and feature of the pneumatically-operated thrombectomy catheter deployment system is a high pressure pump which on the downstroke is capable of delivering fluid at pressures from 100-20,000 psi via the principle of amplification.

Having thus briefly described an embodiment of the present invention and having mentioned some significant aspects and features of the present invention, it is the principal object of the present invention to provide a pneumatically-operated thrombectomy catheter deployment system.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1:
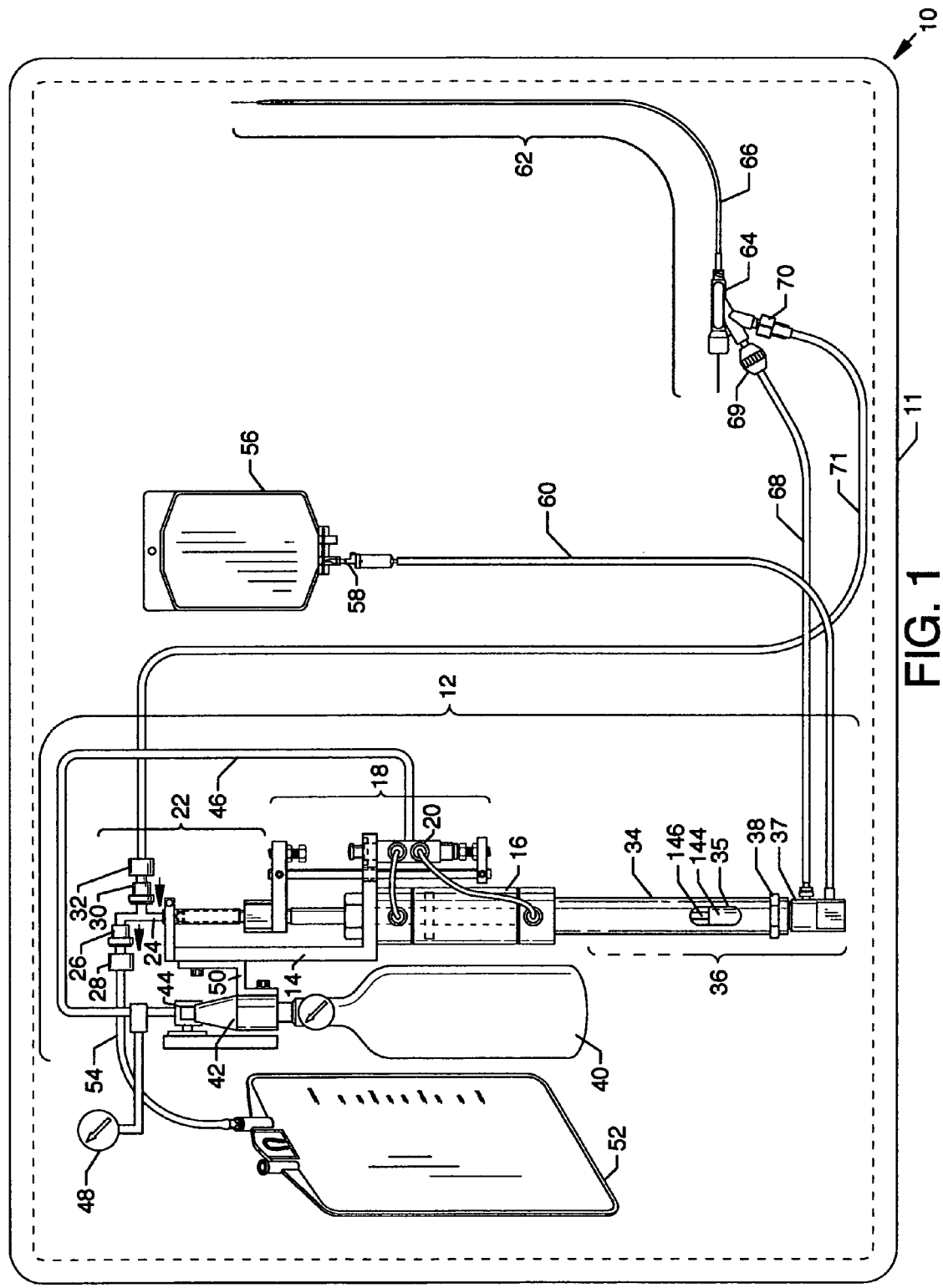
FIG. 1 is a plan view of a pneumatically-operated thrombectomy catheter deployment system, the present invention.

FIG. 1 is a plan view of the pneumatically-operated thrombectomy catheter deployment system 10, the present invention. The pneumatically-operated thrombectomy catheter deployment system 10 preferably includes a sterile package 11 schematically represented such as a sterile bag or other suitable sterile enclosure within the skill known in the art and multiple components synergistically operating to provide operating fluids and sufficient fluid operating pressures and to provide for removal of effluent involved in thrombectomy procedures incorporating the present invention. A major assembly of the present invention includes a centrally located drive unit 12 about which a plurality of components are attached and operated. The drive unit 12 includes a frame 14, a centrally located pneumatically-operated double-acting air cylinder 16 secured to the lower portion of the frame 14, a reciprocating assembly 18 slidingly engaging the frame 14 including a four-way valve 20 secured to the lower portion of the frame 14, an effluent pump 22 secured at the upper portion of the reciprocating assembly 18 and at the upper portion of the frame 14, such effluent pump 22 including a manifold 24, a check valve 26 connected to the outlet of the manifold 24, a check valve 30 connected to the inlet of the manifold 24, as well as a piston and a cylinder described later in detail. The drive unit 12 also includes a housing 34 secured to the lower portion of the double-acting air cylinder 16, an inspection window 35 in the lower region of the housing 34 for pump priming observation, a high pressure pump 36 including a portion aligned in the lower portion of the housing 34 and another portion including a pump base 37 which extends below and beyond the lower portion of the housing 34, a retainer clip 38 securing the high pressure pump 36 to and within the housing 34, a compressed air tank 40, a regulator/connector 42, a valve 44, a compressed air supply tube 46 connecting between the valve 44 and the four-way valve 20, an optional system pressure gauge 48 incorporated in the compressed air supply tube 46, if desired, a bracket 50, and hardware securing the regulator/connector 42 and the compressed air tank 40 to the frame 14.

The plurality of components attached to or utilized in combination with the drive unit 12 include those components now described. An effluent collection bag 52 is connected to the check valve 26 of the effluent pump 22 by an effluent tube 54 and a connector 28. A saline supply bag 56 is connected to the pump base 37 of the high pressure pump 36 by a saline bag spike 58 and a saline supply tube 60. Other major components, assemblies or other features of the present invention include a thrombectomy catheter 62 having a manifold 64 and a catheter tube 66 connected to one end thereof. A high pressure saline delivery tube 68 connects between the pump base 37 of the high pressure pump 36 and the manifold 64 using a connector 69, and a connector 70 connects an effluent tube 71 to the effluent pump 22 through a connector 32.

Figure 2:
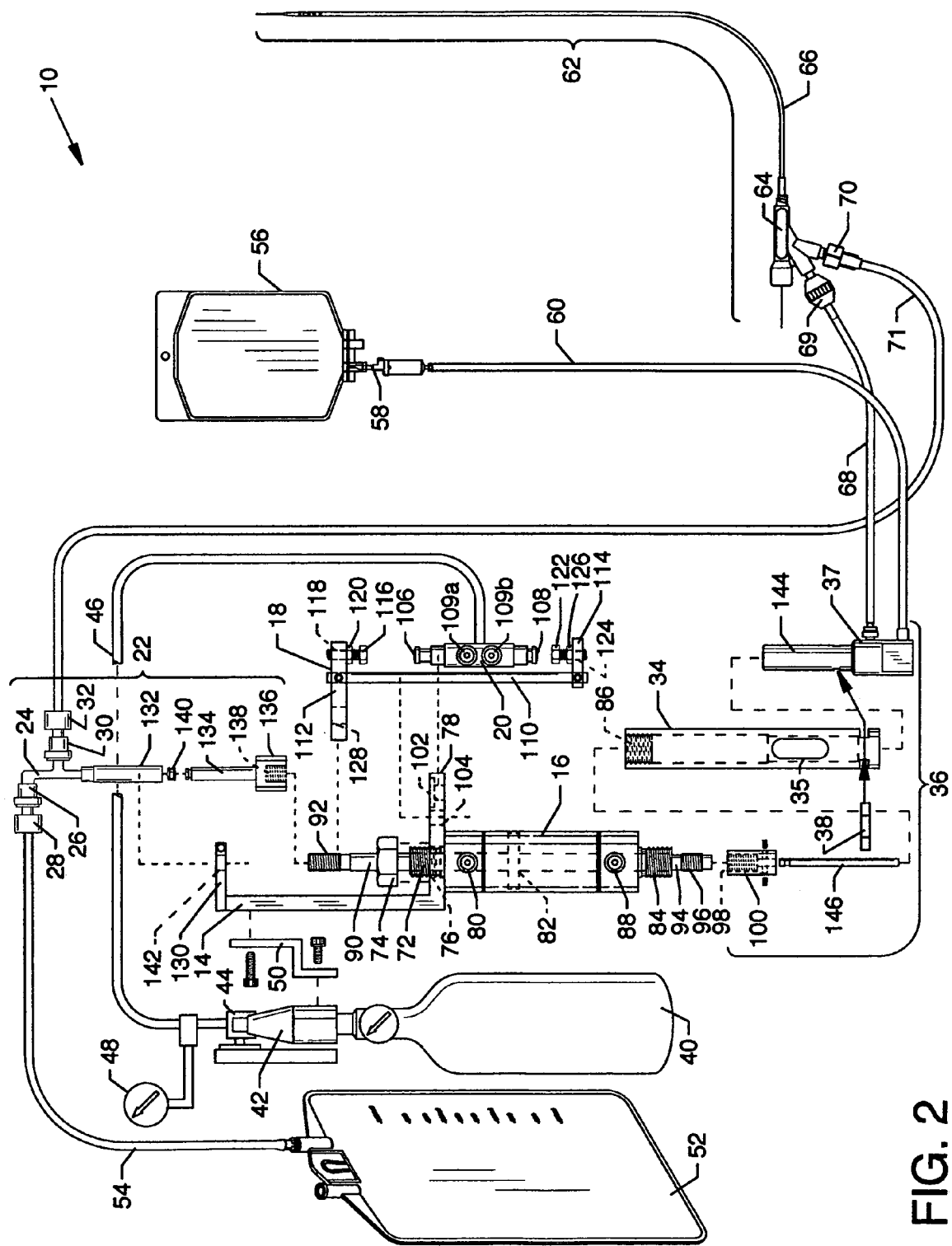
FIG. 2 is a semi-exploded plan view of the pneumatically-operated thrombectomy catheter deployment system.
Figure 3:
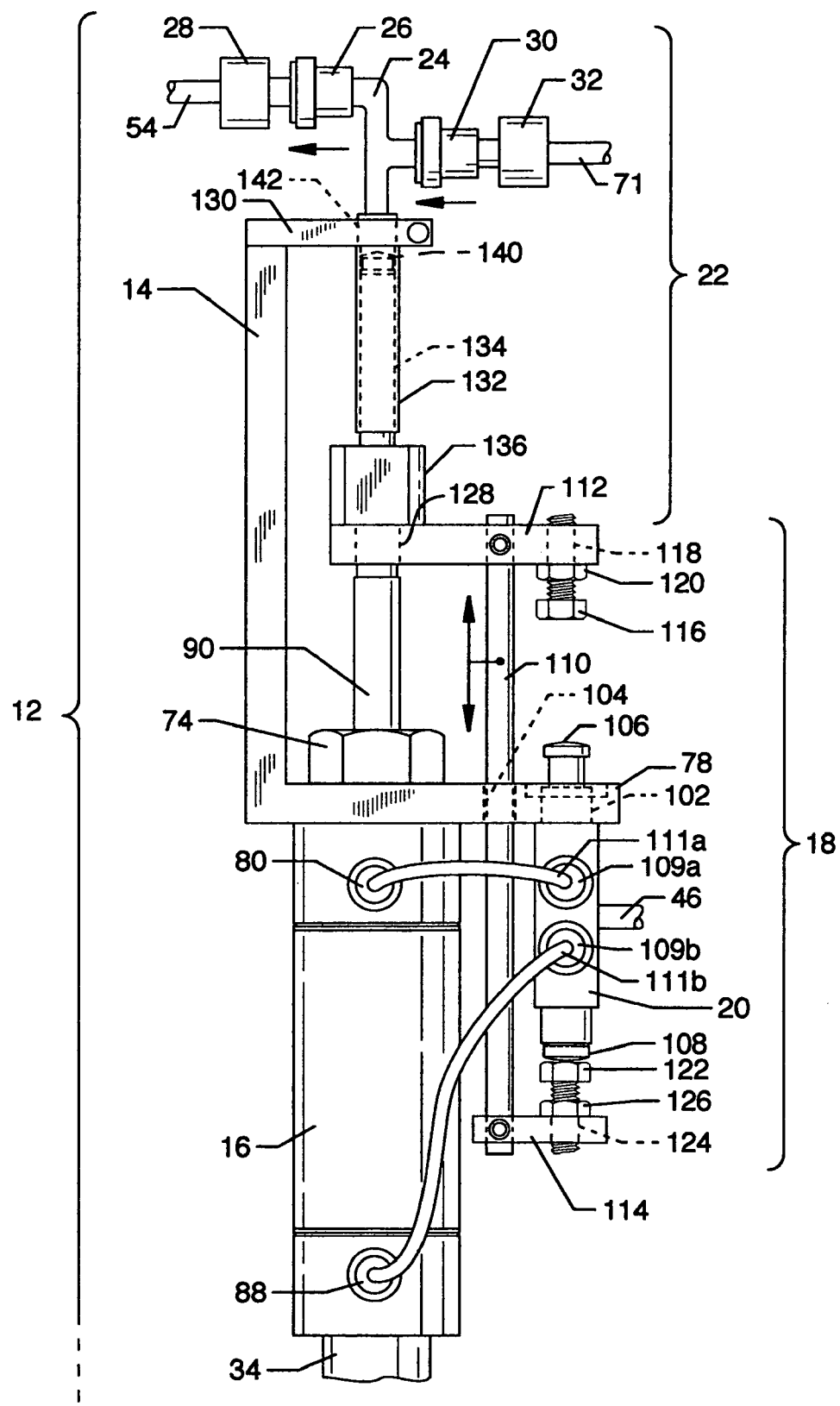
FIG. 3 is a detail view showing the relationship of a frame, a double-acting air cylinder, a reciprocating assembly, a four-way valve, an effluent pump, and other closely associated components.

FIG. 2 is a semi-exploded plan view of the pneumatically-operated thrombectomy catheter deployment system 10 especially showing the features of the double-acting air cylinder 16 and components closely associated therewith, and FIG. 3 is a detail view showing the relationship of the frame 14, the double-acting air cylinder 16, the reciprocating assembly 18, the four-way valve 20, the effluent pump 22, and other closely associated components. Components of the centrally located double-acting air cylinder 16 interact directly with components of the reciprocating assembly 18 and indirectly through related interfacing with the four-way valve 20, whereby alternating direction operation of the double-acting air cylinder 16 is provided first in one direction and then in an opposite direction. Such alternating operation of the double-acting air cylinder 16 provides for powered operation of the high pressure pump 36 and the effluent pump 22.

With reference to FIG. 2 and/or FIG. 3, the invention is further described. The upper end of the double-acting air cylinder 16 includes a threaded fitting 72 having a central bore, wherein such threaded fitting 72 secures by the assistance of a nut 74 within a mounting hole 76 in the horizontally aligned bottom mounting bar 78 of the frame 14 to securely mount the double-acting air cylinder 16 thereto. A port 80 is included at the upper region of the double-acting air cylinder 16 for communication with the top side of a piston 82 (shown in dashed lines) located within the interior of the double-acting air cylinder 16. The lower end of the double-acting air cylinder 16 includes a threaded fitting 84 having a bore, wherein such threaded fitting 84 is incorporated to engage interior threads 86 at the top of the housing 34 to mount the housing 34 to the bottom of the double-acting air cylinder 16. A port 88 is included at the lower portion of the double-acting air cylinder 16 for communication with the bottom side of the piston 82 located within the interior of the double-acting air cylinder 16. A top rod 90 having threads 92 at the upper end thereof extends from the connected piston 82 through the central bore of the threaded fitting 72 passing nonrestrictively through the nut 74; and a bottom rod 94 having threads 96 at the lower end thereof extends from the connected piston 82 through the bore of the threaded fitting 84 to threadingly engage the interior threads 98 of a coupling 100.

The bottom mounting bar 78 also includes an outboard mounting hole 102 and a centrally located hole 104, the latter of which is incorporated for sliding accommodation of the reciprocating assembly 18. The outboard mounting hole 102 is used to frictionally engage and mount an upper portion of the four-way valve 20 to the bottom mounting bar 78. The four-way valve 20 includes a depressible top return actuator 106, an opposed depressible bottom return actuator 108, and inlet/outlet ports 109a-109b. The top return actuator 106 and the opposed bottom return actuator 108 are extensions of the inner components of the four-way valve 20 and are positioned unitarily to operate the four-way valve 20. As shown in simplified graphic form in FIG. 6a and FIG. 6b, an inlet port 109c and vent ports 109d and 109e are also distributed along and about the body of the four-way valve 20. A pneumatic line 111a connects the inlet/outlet port 109a of the four-way valve 20 to the port 80 of the double-acting air cylinder 16, and a pneumatic line 111b connects the inlet/outlet port 109b of the four-way valve 20 to the port 88 of the double-acting air cylinder 16. The reciprocating assembly 18 which interacts with the four-way valve 20 includes a vertically oriented rod 110, a horizontally aligned top actuator bar 112 secured to and extending from the top of the rod 110, and an opposed bottom actuator bar 114 secured to and extending from the bottom of the rod 110. The reciprocating assembly 18 also includes a top travel adjuster bolt 116 which threadingly engages a threaded hole 118 of the top actuator bar 112 and is held and locked in frictional engagement therein by a lock nut 120 which is in alignment with the top return actuator 106 of the four-way valve 20. The reciprocating assembly 18 also includes a bottom travel adjuster bolt 122 which threadingly engages a threaded hole 124 of the bottom actuator bar 114 and is held and locked in frictional engagement therein by a lock nut 126 which is in alignment with the bottom return actuator 108 of the four-way valve 20. The horizontally aligned top actuator bar 112 also includes a vertically aligned hole 128 which fits over and is engaged by the upper portion of the top rod 90 and is secured appropriately thereto, thus connecting the reciprocating assembly 18 to the top rod 90 of the double-acting air cylinder 16.

The effluent pump 22 secures to the top rod 90 of the double-acting air cylinder 16 and to a horizontally aligned top mounting bar 130 of the upper region of the frame 14. The effluent pump 22 includes a pump cylinder 132, a piston 134 continuously formed to include a coupling 136 with internal threads 138, a seal 140 mounted to the top of the piston 134, the manifold 24, and the check valves 26 and 30. The top outer portion of the pump cylinder 132 mountingly secures in a hole 142 in the top mounting bar 130, and the bore of the pump cylinder 132 sealingly aligns to and communicates with the interior of the manifold 24 and components connected thereto. The internal threads 138 of the coupling 136 engage the threads 92 at the top of the top rod 90 in order to mount the lower end of the effluent pump 22 to the top rod 90 of the double-acting air cylinder 16. The piston 134 and seal 140 engage the bore of the pump cylinder 132 and are reciprocatingly operated therein, as later described in detail, to assist in the conveyance of effluent waste from the thrombectomy catheter 62 to the effluent collection bag 52.

Figure 4:
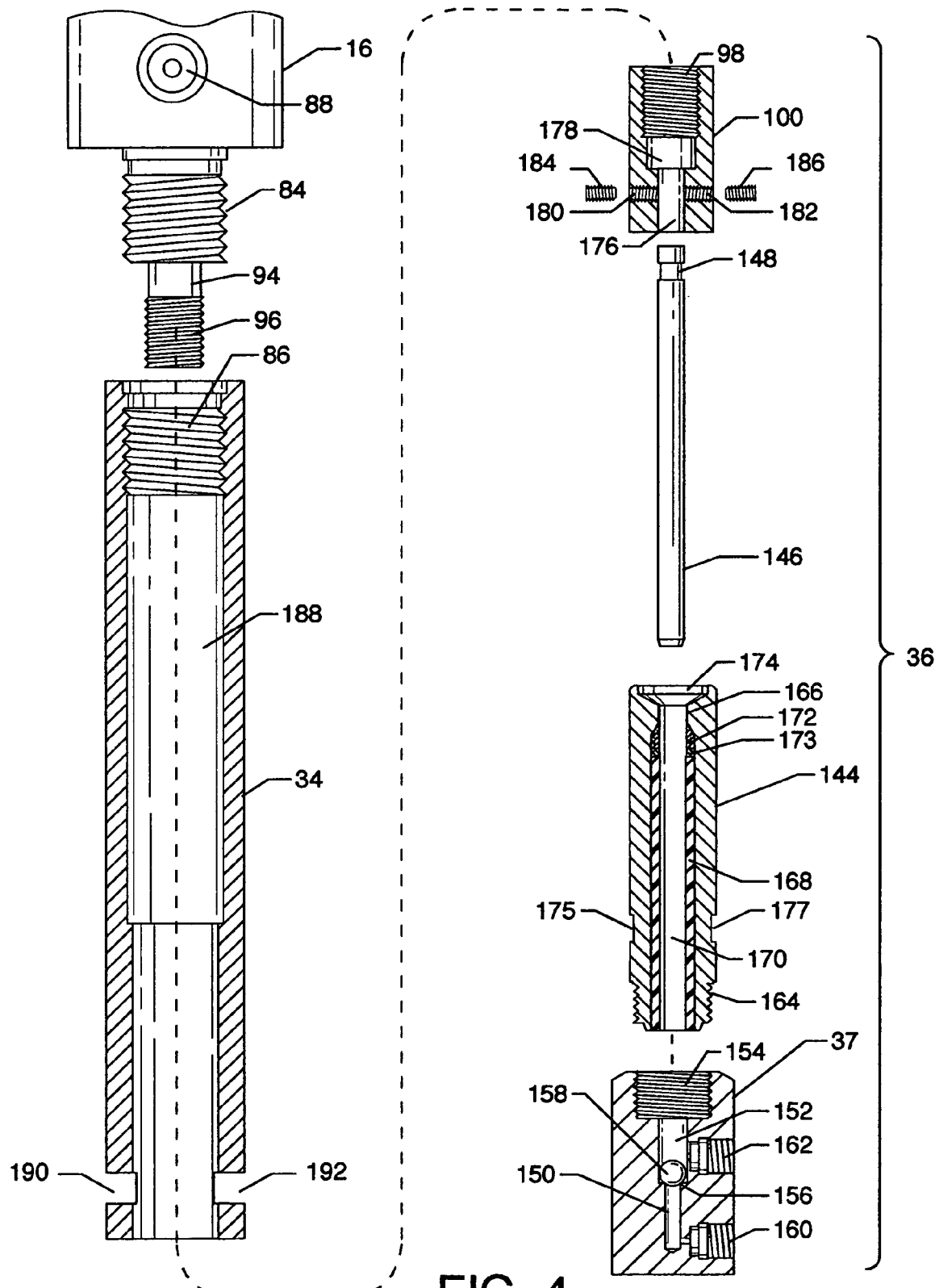
FIG. 4 is an exploded view partly in cross section of structure comprising a high pressure pump, a housing, and the lower portion of the double-acting air cylinder.
Figure 5:
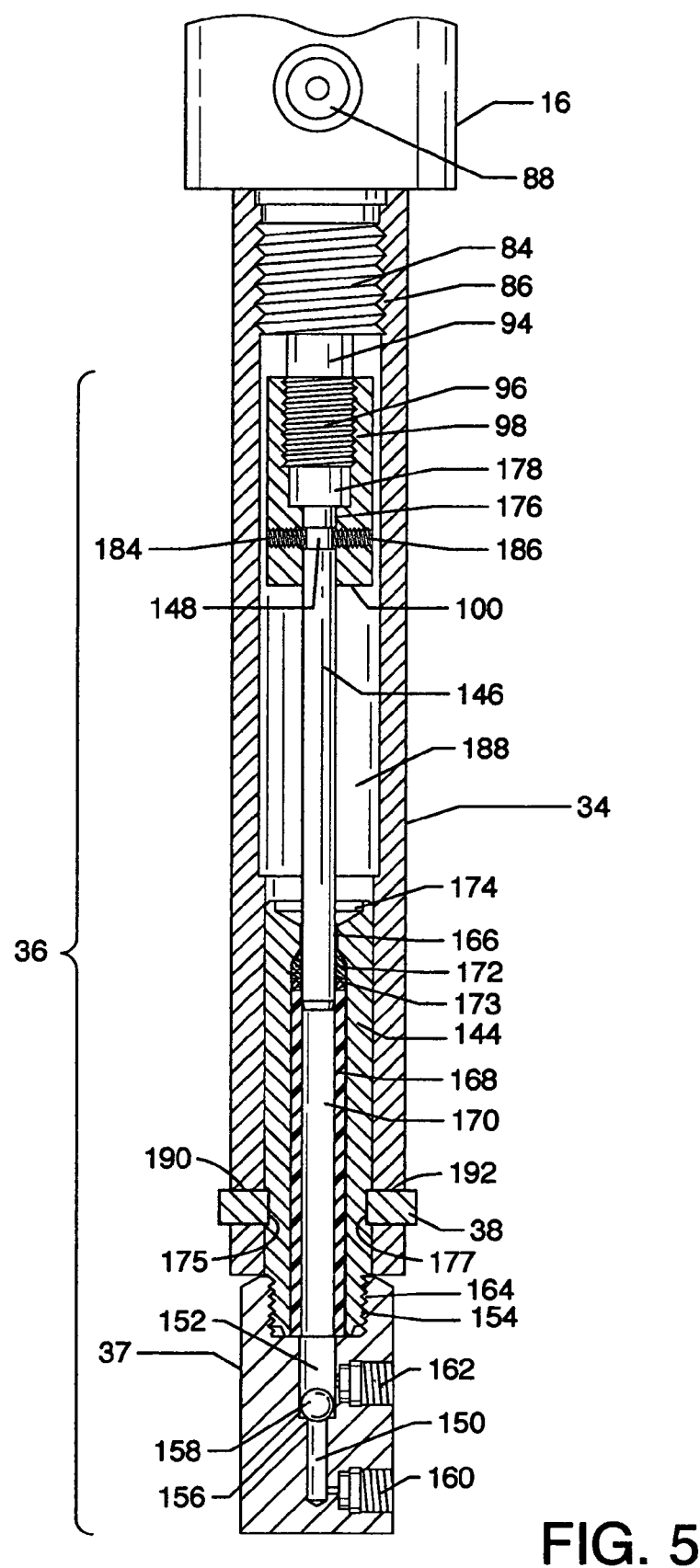
FIG. 5 is a view of the assembled components of FIG. 4.

FIG. 4 is an exploded view partly in cross section of the structure comprising the high pressure pump 36, the housing 34 which is closely associated with the high pressure pump 36, and the lower portion of the double-acting air cylinder 16. The housing 34 mounts to the lower portion of the double-acting air cylinder 16, and a greater portion of the high pressure pump 36 mounts within the housing 34. FIG. 5 is a view of the assembled components of FIG. 4. With reference to FIGS. 2, 4 and 5, the high pressure pump 36 and the housing 34 are now described. The main and readily viewable components of the high pressure pump 36 include the pump base 37, a pump cylinder 144 mounted in the upper portion of the pump base 37 and extending therefrom, a piston 146 having an annular groove 148 at the upper portion thereof, and the coupling 100, such components mounting within or extending from the housing 34. The pump base 37 includes multiple connecting aligned bores of ascendingly larger sizes extending along and about the vertical axis thereof including bottom bore 150, a middle bore 152, and a top bore 154 which is threaded. An annular seat 156 is formed at the intersection of the bottom bore 150 and the middle bore 152 to accommodate a check ball 158 which can be urged vertically along the middle bore 152 during action of the high pressure pump 36. An inlet port 160 communicates directly with the bottom bore 150 and an outlet port 162 communicates directly with the middle bore 152. The threads of the top bore 154 are utilized for connected accommodation of threads 164 at the lower portion of the pump cylinder 144 to suitably seal and secure therewithin, as best shown in FIG. 5. The pump cylinder 144 includes a multiple radius central bore 166 which accommodates a cylindrical liner 168 having a bore 170, which preferably is plastic but which could be of other suitable material. The upper portion of the multiple radius central bore 166 also accommodates a seal 172 and a seal 173 aligned to the top of the cylindrical liner 168. A saline reservoir 174, being part of the multiple radius central bore 166, is located at the top of the pump cylinder 144 for observation of saline during priming of the high pressure pump 36 and for containment of saline which is used for lubrication of the piston 146 and the bore 170 of the cylinder liner 168. The piston 146 extends along the centerline of the pump cylinder 144 and, more specifically, engagingly extends directly through the saline reservoir 174, the top portion of the multiple radius central bore 166, the seal 172, the seal 173, and the bore 170 of the cylinder liner 168 and indirectly through the lower portion of the multiple radius central bore 166. Horizontally aligned flats 175 and 177 are included in the lower region of the pump cylinder 144. The coupling 100 is fashioned to accommodate the upper end of the piston 146 and includes multiple connecting aligned bores of ascendingly larger sizes extending along and about the vertical axis thereof, including a bottom bore 176, and a top bore 178, and also includes the interior threads 98 extending upwardly from the top bore 178. Opposed horizontally aligned threaded holes 180 and 182 intersect the bottom bore 176 and are utilized to accommodate set screws 184 and 186. The set screws 184 and 186 engage the annular groove 148 of the piston 146 in order to secure the piston 146 in the bottom bore 176 of the coupling 100. The housing 34 has a multiple radius bore 188 and includes the interior threads 86 at the top portion thereof for threaded accommodation of the threaded fitting 84 at the bottom of the double-acting air cylinder 16. Opposed grooves 190 and 192 are included at the lower exterior of the housing 34 for alignment with the flats 175 and 177 at the lower region of the pump cylinder 144 and for accommodation of the retainer clip 38. The retainer clip 38 lockingly intersects the grooves 190 and 192 of the housing 34 and the flats 175 and 177 of the pump cylinder 144 to secure the high pressure pump 36 within the multiple radius bore 188 of the housing 34.

Figure 6A:
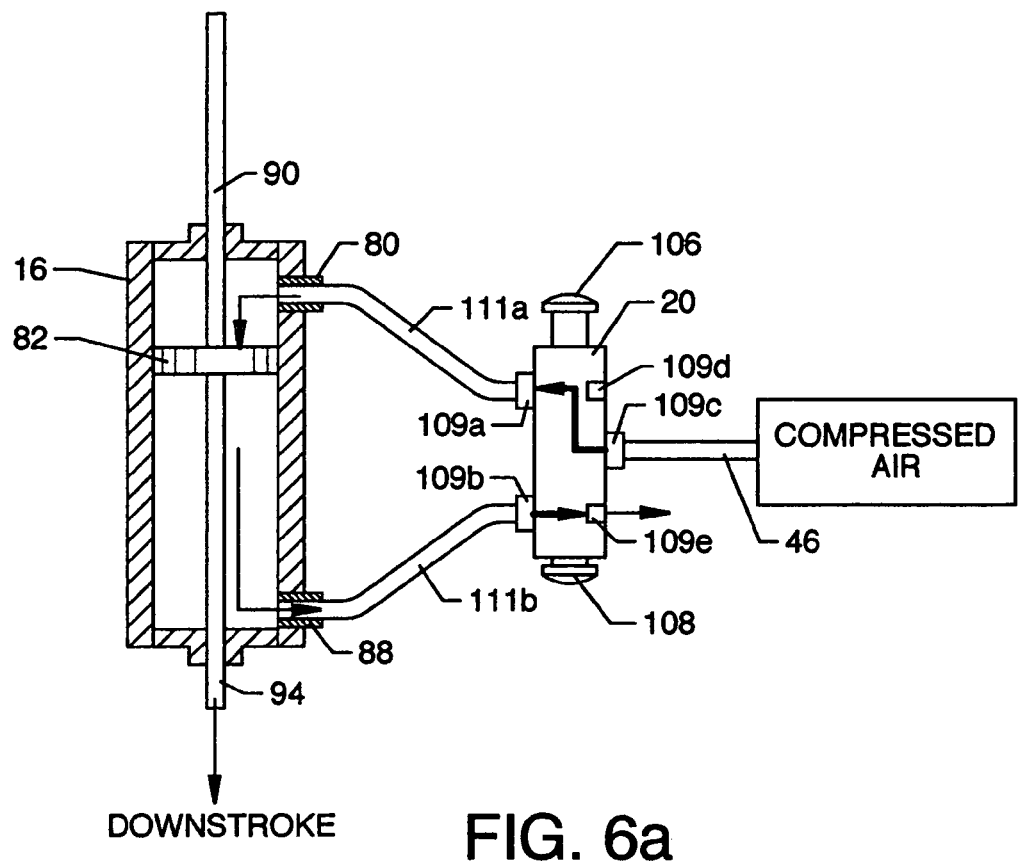
FIG. 6a and FIG. 6b are schematic views showing the relationship of the four-way valve to the double-acting air cylinder.
Figure 6B:
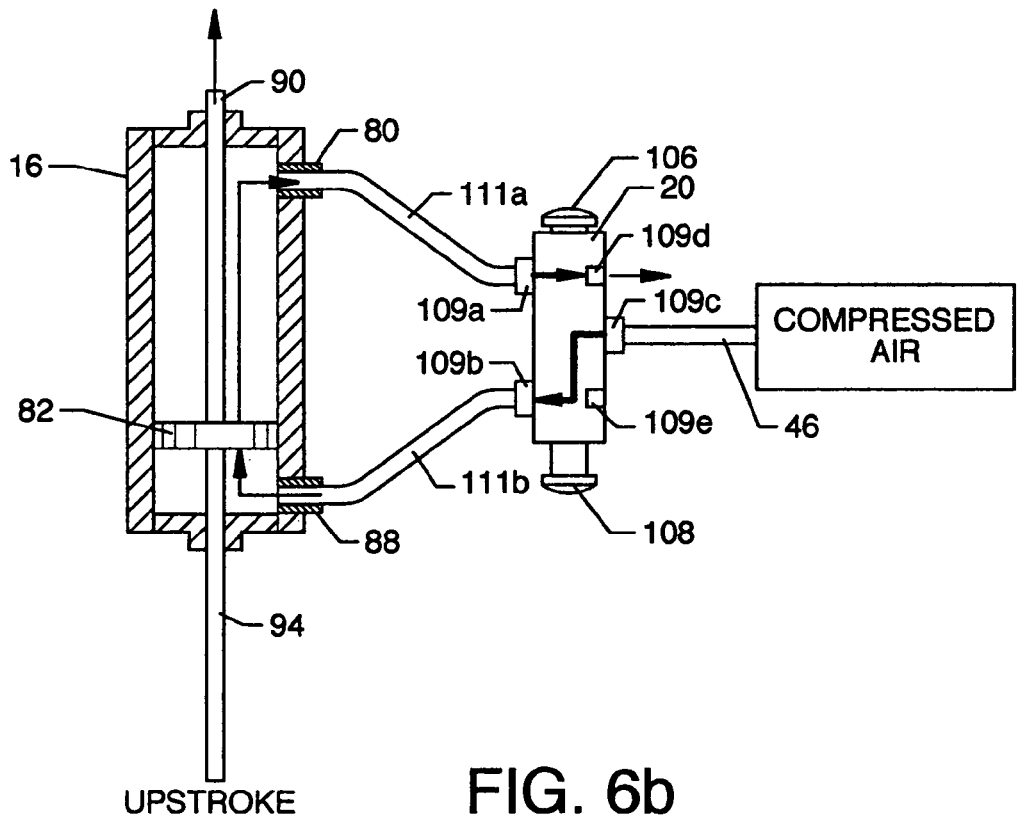

FIG. 6a and FIG. 6b are schematic views showing the relationship of the four-way valve 20 to the double-acting air cylinder 16, wherein FIG. 6a shows the piston downstroke mode, and FIG. 6b shows the piston upstroke mode. Operation of such components is described in detail in the mode of operation.

Mode of Operation

With reference to FIGS. 1, 2, 3, 4, 5, 6a and 6b, the mode of operation of the pneumatically-operated thrombectomy catheter deployment system 10 is now described. First, the sterile package 11 containing the balance of the pneumatically-operated thrombectomy catheter deployment system 10 is opened and a sterile exchange to hand off the catheter and other components to a sterile technician is accomplished followed by suspension of the components from an IV stand or other suitable support. This is followed by spiking a heparinized saline supply bag 56 with the saline bag spike 58, priming the high pressure pump 36, and then submerging the catheter tip of the thrombectomy catheter 62 in a bowl of sterile saline and operating the drive unit 12 to prime the catheter tube 66 and associated components. Priming of the high pressure pump 36 is accompanied by removing the retainer clip 38 and maneuvering the pump base 37 and the pump cylinder 144 downwardly to disengage the piston 146 from the upper region of the bore 170 of the pump cylinder 144 as observed through the inspection window 35. Uninterrupted bubble-free saline flow observed at the saline reservoir 174 as supplied through the saline supply tube 60 subsequent to saline spiking indicates proper priming of the high pressure pump 36 whereupon the pump cylinder 144 and pump base 37 are unitarily urged upwardly for re-engagement of the piston 146. The retainer clip 38 is re-engaged to secure the pump base 37 and the pump cylinder 144 within the lower portion of the housing 34. The valve 44 atop the regulator/connector 42 is then utilized as required to allow compressed air from the compressed air tank 40 (or from an alternative stationary supply) to be delivered to the compressed air supply tube 46 for communication with the inlet port 109c on the rear of the four-way valve 20. In the alternative, the valve 44 can be replaced by a valve which can be operated by a foot pedal. Consider that the invention is shown in vertical orientation and that the invention could also be horizontally oriented and supported in the horizontal plane. Description of the invention is offered with respect to vertical orientation, but the principle of operation remains the same for either orientation.

Operation of the four-way valve 20 and the reciprocating assembly 18 occurs as next set forth. Consider first the downstroke mode and proper upwardly shuttled positioning of the inner components of the four-way valve 20, and thus of internal paths within the four-way valve 20, to provide appropriate internal paths within the four-way valve 20, as shown with reference to schematic FIG. 6a. Compressed air is delivered to the four-way valve 20 through the inlet port 109c, passes through the four-way valve 20, exits through the inlet/outlet port 109a, and thence passes through the pneumatic line 111a and the port 80 to the interior of the double-acting air cylinder 16. The compressed air communicates with the top of the piston 82 to drive the piston 82, the top rod 90, the bottom rod 94, and attached components downwardly toward the housing 34. During such downstroke mode activity, air residing in the double-acting air cylinder 16 in communication with the bottom of the piston 82 is expellingly vented from the lower region of the double-acting air cylinder 16 via the port 88, the pneumatic line 111b, the inlet/outlet port 109b, and the vent port 109e in the four-way valve 20.

During the downstroke mode, the reciprocating assembly 18 attached to the top rod 90 is repositioned downwardly until the top travel adjuster bolt 116 on the top actuator bar 112 of the reciprocating assembly 18 contacts and urges the top return actuator 106 of the four-way valve 20 downwardly to reposition the inner components of the four-way valve 20. During such repositioning and shuttling of the inner components of the four-way valve 20, internal paths within the four-way valve 20 are positioned to provide appropriate internal paths within the four-way valve 20, as shown with reference to schematic FIG. 6b, to reverse the flow of compressed air within the double-acting air cylinder 16 to provide for upstroke mode activity. Compressed air is delivered to the four-way valve 20 through the inlet port 109c, passes through the repositioned four-way valve 20, exits through the inlet/outlet port 109b, and thence passes through the pneumatic line 111b and the port 88 to the interior of the double-acting air cylinder 16. The compressed air communicates with the bottom of the piston 82 to drive the piston 82, the top rod 90, the bottom rod 94, and attached components upwardly toward the top mounting bar 130 of the frame 14. During such upstroke mode activity, air residing in the double-acting air cylinder 16 in communication with the top of the piston 82 is expellingly vented from the upper region of the double-acting air cylinder 16 via the port 80, the pneumatic line 111a, the inlet/outlet port 109a, and the vent port 109d in the four-way valve 20. Such upstroke mode activity continues until the bottom travel adjuster bolt 122 on the bottom actuator bar 114 of the reciprocating assembly 18 contacts and urges the bottom return actuator 108 of the four-way valve 20 upwardly to the position indicated in FIG. 6a, once again repositioning the inner components of the four-way valve 20, wherein downstroke mode activity, as previously described, is once again initiated.

Operation of the high pressure pump 36 and the effluent pump 22 occurs as next set forth. Downstroke and upstroke mode activity provides for operation of the effluent pump 22 and the high pressure pump 36, although the intake and compression cycles of the respective pumps are diametrically opposed. Pressures of the high pressure pump 36 can be produced according to the principle of amplification in the range of 200 to 20,000 psi for use in thrombectomy procedures using an attached thrombectomy catheter, such as the attached thrombectomy catheter 62. Saline from the saline supply bag 56 is available and delivered through the saline bag spike 58 and the saline supply tube 60 to the inlet port 160 of the pump base 37. During the upstroke mode activity, the check ball 158 is urged upwardly and saline fluid is drawn into the bore 170 of the pump cylinder 144 by the influence of the low pressure creating action of the upwardly moving piston 146 of the high pressure pump 36 until the upward travel of the piston 146 is reversed by interaction of the reciprocating assembly 18 with the bottom return actuator 108 to reposition the four-way valve 20. Subsequent to the reciprocating reversal of the piston 146 due to action by the four-way valve 20, the check ball 158 is reseated on the annular seat 56 and the piston 146 is compressingly and forcibly urged downwardly to provide high pressure saline to the outlet 162 of the pump base 37 for delivery through the high pressure saline delivery tube 68 and the connector 69 to the manifold 64 and thence the catheter tube 66 of the thrombectomy catheter 62. Such compressive downstroke activity continues until the top travel adjuster bolt 116 on the top actuator bar 112 of the reciprocating assembly 18 contacts and urges the top return actuator 106 of the four-way valve 20 downwardly to the position indicated in FIG. 6b to reposition the inner components of the four-way valve 20, wherein upstroke mode activity, as previously described, is once again initiated. With respect to effluent flow, effluent forcibly urged from the thrombectomy catheter 62 by the internal pressures as created by the flow of pressurized saline therein is made available to the effluent pump 22 through the manifold 64, the connector 70, the effluent tube 71, and the connector 32, and is assisted in flow therefrom by action of the effluent pump 22. During downstroke mode activity, as previously described, the piston 134 of the effluent pump 22, which is connected to the top actuator bar 112 of the reciprocating assembly 18, moves downwardly within the pump cylinder 132 creating a vacuum, thereby allowing and thereby drawing effluent through the check valve 30 into the interior of the pump cylinder 132. Then, during upstroke mode activity, as previously described, the piston 134 is moved upwardly, thereby forcibly ejecting the effluent from the pump cylinder 132 whilst at the same time the outward effluent flow closes the check valve 30 and opens the check valve 26, wherein effluent is forcibly urged along the effluent tube 54 into the effluent collection bag 52 until downstroke mode activity reverses the direction of the piston 134 to travel downwardly to once again begin the intake of effluent into the effluent pump 22. In the alternative, a roller pump assembly driven by the reciprocating assembly 18 could be substituted in lieu of the effluent pump 22. During reciprocating operation of the pneumatically-operated thrombectomy catheter deployment system 10, downstroke mode activity causes the high pressure pump 36 to pressurize and expel saline and causes the effluent pump 22 to receive effluent, and upstroke mode activity causes the high pressure pump 36 to receive saline and causes the effluent pump 22 to pressurize and expel effluence. If a stationary compressed air supply is available, the compressed air tank 40 can be removed and the stationary compressed air supply can be connected to the regulator/connector 42. Operating speed of the invention is influenced by several factors. Pressure delivered to the four-way valve 20, and thus to the double-acting air cylinder 16, can be adjusted by metering the valve 44 to control the force and operating speed of the double-acting air cylinder 16. Vertical operation limits of the piston 82, and thus of the high pressure pump 36 and the effluent pump 22, as well as operational force, can be influenced by adjustment of the top travel adjuster bolt 116 and the bottom travel adjuster bolt 122. The compressive loads of the high pressure pump 36 and of the effluent pump 22 in the downstroke mode and the upstroke mode are staggered such that compression occurs only in one pump at a time to spread and conserve the use of compressed air, thereby allowing the use of a practical sized compressed air tank 40 as opposed to a regime where simultaneously occurring compressive loads would require a larger compressed air tank. Throughout the foregoing description, operation has been described in terms of utilizing compressed air. It should be understood, however, that nitrogen or other suitable gas could be employed in lieu of air.

Various modifications can be made to the present invention without departing from the apparent scope thereof.

Pneumatic Drive Unit

Parts List

- 10 pneumatically-operated thrombectomy catheter deployment system
- 11 sterile package
- 12 drive unit
- 14 frame
- 16 double-acting air cylinder
- 18 reciprocating assembly
- 20 four-way valve
- 22 effluent pump
- 24 manifold
- 26 check valve
- 28 connector
- 30 check valve
- 32 connector
- 34 housing
- 35 inspection window
- 36 high pressure pump
- 37 pump base
- 38 retainer clip
- 40 compressed air tank
- 42 regulator/connector
- 44 valve
- 46 compressed air supply tube
- 48 pressure gauge
- 50 bracket
- 52 effluent collection bag
- 54 effluent tube
- 56 saline supply bag
- 58 saline bag spike
- 60 saline supply tube
- 62 thrombectomy catheter
- 64 manifold
- 66 catheter tube
- 68 high pressure saline delivery tube
- 69 connector
- 70 connector
- 71 effluent tube
- 72 threaded fitting
- 74 nut
- 76 mounting hole
- 78 bottom mounting bar
- 80 port
- 82 piston
- 84 threaded fitting
- 86 interior threads
- 88 port
- 90 top rod
- 92 threads
- 94 bottom rod
- 96 threads
- 98 interior threads
- 100 coupling
- 102 mounting hole
- 104 centrally located hole
- 106 top return actuator
- 108 bottom return actuator
- 109*a-b* inlet/outlet ports
- 109*c* inlet port
- 109*d-e* vent ports
- 110 rod
- 111*a-b* pneumatic lines
- 112 top actuator bar
- 114 bottom actuator bar
- 116 top travel adjuster bolt
- 118 threaded hole
- 120 lock nut
- 122 bottom travel adjuster bolt
- 124 threaded hole
- 126 lock nut
- 128 hole
- 130 top mounting bar
- 132 pump cylinder
- 134 piston
- 136 coupling
- 138 internal threads
- 140 seal
- 142 hole
- 144 pump cylinder
- 146 piston
- 148 annular groove
- 150 bottom bore
- 152 middle bore
- 154 top bore
- 156 annular seat
- 158 check ball
- 160 inlet port
- 162 outlet port 164 threads
166 multiple radius central bore
168 cylinder liner
170 bore
172 seal
173 seal
174 saline reservoir
175 flat
176 bottom bore
177 flat
178 top bore
180 threaded hole
182 threaded hole
184 set screw
186 set screw
188 multiple radius bore
190 groove
192 groove It is claimed:

1. A pneumatically-operated thrombectomy catheter deployment system comprising a prepackaged disposable combination of:
   a. a thrombectomy catheter drive unit connected to a nondisposable compressed gas source, the drive unit including:
      (1) a double-acting air cylinder;
      (2) a four-way valve having two inlet/outlet ports that direct-compressed gas from the nondisposable compressed gas source to influence directional operation of the double-acting air cylinder, and two vent ports that vent the compressed gas into air; the four-way valve also having a separate inlet port for the compressed gas; and
      (3) a frame that is simultaneously connected to the double-acting air cylinder, the four-way valve, an effluent pump, and a pressure regulator for the compressed gas source, said frame securing a close vertical alignment between the effluent pump, the double-acting air cylinder, and a high pressure pump connected to a source of fluid, said frame further comprising at least one traveler bolt that ensures proper alignment of the four-way valve and the double-acting air cylinder;
   b. the effluent pump opposing the high pressure pump such that both are operated by the double-acting air cylinder and maintain isovolumetric flow of the fluid being pumped into and then out of a patient, and
   c. a thrombectomy catheter having a distal portion and a proximal portion, said proximal portion being operatively connected to the thrombectomy catheter drive unit and the effluent pump such that the fluid is supplied to the thrombectomy catheter and said fluid emanates from the distal portion of the thrombectomy catheter at an increased pressure in a cross stream flow pattern.

2. The pneumatically-operated thrombectomy catheter deployment system of claim 1, wherein the compressed gas is selected from the group consisting of compressed air and compressed nitrogen.

3. The pneumatically-operated thrombectomy catheter deployment system of claim 2, wherein the nondisposable compressed gas source is selected from the group consisting of a portable compressed gas tank and a stationary compressed gas supply.

4. The pneumatically-operated thrombectomy catheter deployment system of claim 1, wherein the high pressure pump has a cycle with an intake stroke and a compression stroke and the effluent pump has a cycle with an intake stroke and a compression stroke and wherein the cycles of the high pressure pump and the effluent pump are diametrically opposed, such that the compression stroke of the high pressure pump and the intake stroke of the effluent pump occur simultaneously and the intake stroke of the high pressure pump and the compression stroke of the effluent pump occur simultaneously.

5. The pneumatically-operated thrombectomy catheter deployment system of claim 1, wherein the high pressure pump produces pressures of from 200 psi to 20,000 psi.

6. The pneumatically-operated thrombectomy catheter deployment system of claim 1, wherein the high pressure pump has a pump base with an inlet and an outlet and the effluent pump has an effluent pump manifold with an inlet and an outlet, the inlet of the pump base and the inlet and outlet of the effluent pump manifold each having a check valve associated therewith.

7. The pneumatically-operated thrombectomy catheter deployment system of claim 1, wherein:
   the thrombectomy catheter has a thrombectomy catheter manifold with a high pressure saline delivery tube connected between the thrombectomy catheter manifold and the high pressure pump and with an effluent tube connected between the thrombectomy catheter manifold and the effluent pump.

8. The pneumatically-operated thrombectomy catheter deployment system of claim 1 wherein the fluid is saline.

9. The pneumatically-operated thrombectomy catheter deployment system of claim 1, further comprising:
   e. an effluent collection device connected to the effluent pump.

10. The pneumatically-operated thrombectomy catheter deployment system of claim 9, wherein the effluent collection device is an effluent collection bag.

11. The pneumatically-operated thrombectomy catheter deployment system of claim 1, wherein the thrombectomy catheter drive unit is sterile and further comprising:
    e. a sterile package enclosing the thrombectomy catheter drive unit.

12. A pneumatically-operated thrombectomy catheter deployment kit comprising:
    a. a sterile package;
    b. a sterile compressed air tank within the sterile package;
    c. a sterile thrombectomy catheter drive unit within the sterile package, the sterile thrombectomy catheter drive unit being connected to the sterile compressed air tank, the drive unit including:
       (1) a double-acting air cylinder;
       (2) a four-way valve having two inlet/outlet ports that direct-compressed gas from the compressed air tank to influence directional operation of the double-acting air cylinder, and two vent ports that vent the compressed gas into air; the four-way valve also having a separate inlet port for the compressed gas; and
       (3) a frame that is simultaneously connected to the double-acting air cylinder, the four-way valve, and effluent pump, and a pressure regulator for the compressed gas source, said frame securing a close vertical alignment between the effluent pump, the double-acting air cylinder, and a high pressure pump connected to a source of fluid, said frame further comprising at least one traveler bolt that ensures proper alignment of the four-way valve and the double-acting air cylinder;
    d. the effluent pump opposing the high pressure pump such that both are operated by the double-acting air cylinder and maintain isovolumetric flow of the fluid being pumped into and then out of a patient; and, e. a sterile thrombectomy catheter within the sterile package, the sterile thrombectomy catheter having a manifold connected to the sterile thrombectomy catheter drive unit, said thrombectomy catheter having a distal portion and a proximal portion, said proximal portion being operatively connected to the thrombectomy catheter drive unit and the effluent pump such that the fluid is supplied to the thrombectomy catheter and said fluid emanates from the distal portion of the thrombectomy catheter at an increased pressure in a cross stream flow pattern.

13. The pneumatically-operated thrombectomy catheter deployment kit of claim 12, further comprising:

f. a sterile effluent collection bag within the sterile package, the sterile effluent collection bag being connected to the sterile thrombectomy catheter drive unit.

14. The pneumatically-operated thrombectomy catheter deployment kin of claim 13, further comprising:

g. a sterile saline supply bag within the sterile package, the sterile saline supply bag being available for connection to the sterile thrombectomy catheter drive unit.

15. A method of deploying a pneumatically-operated thrombectomy catheter comprising the steps of:

a. providing a pneumatically-operated thrombectomy catheter deployment kit including:
  (1) a sterile package;
  (2) a sterile compressed air tank within the sterile package;
  (3) a sterile thrombectomy catheter drive unit within the sterile package, the sterile thrombectomy catheter drive unit being connected to the sterile compressed air tank the drive unit including:
    (A) a double-acting air cylinder;
    (B) a four-way valve having two inlet/outlet ports that direct-compressed gas from the compressed air tank to influence directional operation of the double-acting air cylinder, and two vent ports that vent the compressed gas into air; the four-way valve also having a separate inlet port for the compressed gas; and
    (C) a frame that is simultaneously connected to the double-acting air cylinder, the four-way valve, and effluent pump, and a pressure regulator for the compressed gas source, said frame securing a close vertical alignment between the effluent pump, the double-acting air cylinder, and a high pressure pump connected to a source of fluid, said frame further comprising at least one traveler bolt that ensures proper alignment of the four-way valve and the double-acting air cylinder;
  (4) the effluent pump opposing the high pressure pump such that both are operated by the double-acting air cylinder and maintain isovolumetric flow of the fluid being pumped into and then out of a patient;
  (5) a sterile thrombectomy catheter within the sterile package, the sterile thrombectomy catheter having a manifold connected to the sterile thrombectomy catheter drive unit, said thrombectomy catheter having a distal portion and a proximal portion, said proximal portion being operatively connected to the thrombectomy catheter drive unit and the effluent pump such that the fluid is supplied to the thrombectomy catheter and said fluid emanates from the distal portion of the thrombectomy catheter at an increased pressure in a cross stream flow pattern; and, b. opening the sterile package.

16. The method of claim 15, further comprising the steps of:

c. providing a sterile saline supply bag; and, d. spiking the sterile saline supply bag to connect the sterile saline supply bag to the sterile thrombectomy catheter drive unit.

17. The method of claim 16, further comprising the step of: priming the sterile thrombectomy catheter drive unit to provide bubble-free sterile saline to the sterile thrombectomy catheter.

18. A pneumatically-operated thrombectomy catheter deployment system comprising a prepackaged disposable combination of:

a. a thrombectomy catheter drive unit connected to a disposable compressed gas source, the drive unit including:
  (1) a double-acting air cylinder;
  (2) a four-way valve having two inlet/outlet ports that direct-compressed gas from the disposable compressed gas source to influence directional operation of the double-acting air cylinder, and two vent ports that vent the compressed gas into air; the four-way valve also having a separate inlet port for the compressed gas; and
  (3) a frame that is simultaneously connected to the double-acting air cylinder, the four-way valve, an effluent pump, and a pressure regulator for the compressed gas source, said frame securing a close vertical alignment between the effluent pump, the double-acting air cylinder, and a high pressure pump connected to a source of fluid, said frame further comprising at least one traveler bolt that ensures proper alignment of the four-way valve and the double-acting air cylinder;

b. the effluent pump opposing the high pressure pump such that both are operated by the double-acting air cylinder and maintain isovolumetric flow of the fluid being pumped into and then out of a patient, and c. a thrombectomy catheter having a distal portion and a proximal portion, said proximal portion being operatively connected to the thrombectomy catheter drive unit and the effluent pump such that the fluid is supplied to the thrombectomy catheter and said fluid emanates from the distal portion of the thrombectomy catheter at an increased pressure in a cross stream flow pattern.

19. The pneumatically-operated thrombectomy catheter deployment system of claim 18, wherein the disposable compressed gas source is a sterilized compressed air tank and the sterile thrombectomy catheter drive unit is preconnected to the sterilized compressed air tank and the sterilized compressed air tank is enclosed within the sterile package.

20. The pneumatically-operated thrombectomy catheter deployment system of claim 18, wherein the thrombectomy catheter drive unit is sterile and further comprises:

e. a sterile package enclosing the thrombectomy catheter drive unit.

* * * * *

UNITED STATES PATENT AND TRADEMARK OFFICE
CERTIFICATE OF CORRECTION

| | | |
|---|---|---|
| PATENT NO. | : 7,842,010 B2 | Page 1 of 1 |
| APPLICATION NO. | : 11/294005 | |
| DATED | : November 30, 2010 | |
| INVENTOR(S) | : Bonnette et al. | |

It is certified that error appears in the above-identified patent and that said Letters Patent is hereby corrected as shown below:

ON THE FACE PAGE

On the Face Page, in Field (56), under "OTHER PUBLICATIONS", in Column 2, Line 2, delete "Activity." and insert -- Activity, --, therefor.

IN THE SPECIFICATION

In Column 4, Line 20, delete "unit;" and insert -- unit. --, therefor.

In Column 5, Line 31, delete "EMBODIMENT" and insert -- EMBODIMENTS --, therefor.

In Column 11, Line 44, delete "Pneumatic Drive Unit" and insert -- Pneumatically-Operated Thrombectomy Catheter Deployment System --, therefor.

IN THE CLAIMS

In Column 14, Line 30, delete "e." and insert -- d. --, therefor.

In Column 14, Line 38, delete "e." and insert -- d. --, therefor.

In Column 15, Line 20, in Claim 14, delete "kin" and insert -- kit --, therefor.

In Column 15, Line 34, in Claim 15, delete "tank" and insert -- tank, --, therefor.

In Column 16, Line 14, insert -- e. -- before "priming", therefor.

In Column 16, Line 60, delete "e." and insert -- d. --, therefor.

Signed and Sealed this
Tenth Day of January, 2012

David J. Kappos
*Director of the United States Patent and Trademark Office*